(12) United States Patent
Hacikyan (10) Patent No.: US 9,829,472 B2
(45) Date of Patent: Nov. 28, 2017

(54) PORTABLE HAND-HELD OXYGEN MONITOR

(71) Applicant: Michael Hacikyan, Naples, FL (US)

(72) Inventor: Michael Hacikyan, Naples, FL (US)

( * ) Notice: Subject to any disclaimer, the term of this patent is extended or adjusted under 35 U.S.C. 154(b) by 344 days.

(21) Appl. No.: 14/479,437

(22) Filed: Sep. 8, 2014

(65) Prior Publication Data

US 2016/0069833 A1   Mar. 10, 2016

(51) Int. Cl.
*G01N 1/22* (2006.01)
*G01N 33/00* (2006.01)
*G01N 27/409* (2006.01)
*G01N 1/02* (2006.01)

(52) U.S. Cl.
CPC ............... *G01N 33/00* (2013.01); *G01N 1/22* (2013.01); *G01N 27/409* (2013.01); *G01N 33/0004* (2013.01); *G01N 33/0009* (2013.01); *G01N 33/0062* (2013.01); *G01N 33/0063* (2013.01); *G01N 2001/021* (2013.01); *G01N 2001/2291* (2013.01); *G01N 2033/0068* (2013.01)

(58) Field of Classification Search
None
See application file for complete search history.

(56) References Cited

U.S. PATENT DOCUMENTS

| | | | | |
|---|---|---|---|---|
| 5,479,359 A | * | 12/1995 | Rogero | G01M 3/20 248/206.5 |
| 6,167,766 B1 | * | 1/2001 | Dunn | G01N 1/18 73/863.01 |
| 2002/0009119 A1 | * | 1/2002 | Matthew | G01N 33/0009 374/45 |
| 2003/0173205 A1 | * | 9/2003 | Karlsson | B01J 8/008 203/1 |
| 2007/0035255 A1 | * | 2/2007 | Shuster | G08B 7/06 315/200 R |
| 2007/0107594 A1 | * | 5/2007 | Piccinini | B01D 53/22 95/52 |

(Continued)

OTHER PUBLICATIONS

Neutronics Inc., "Model OA-1S+ Portable Ultra-Trace Oxygen Analyzer Operations Manual", Oct. 2004, 29 pages.

(Continued)

*Primary Examiner* — R. A Smith
*Assistant Examiner* — Herbert K Roberts
(74) *Attorney, Agent, or Firm* — Walter W. Duft (57) ABSTRACT

A portable hand-held oxygen monitor for monitoring oxygen in a weld zone includes a user interface having an alphanumeric display and one or more user interface buttons. An audiovisual alarm includes an indicator light and an audio output device, the indicator light being separate and distinct from the alphanumeric display. The oxygen monitor implements an oxygen monitoring mode responsive to activation of one or more of the user interface buttons, wherein (1) a gas sample is obtained, (2) a digital gas sample oxygen level value is generated, and (3) the gas sample oxygen level value is compared to a stored oxygen level alarm value, and the audiovisual alarm is activated if the gas sample oxygen level value is less than the oxygen level alarm value. The activating includes illuminating the indicator light and generating sound from the audio output device to alert a monitor user that is safe to weld.

20 Claims, 4 Drawing Sheets

(56) References Cited

U.S. PATENT DOCUMENTS

2013/0244336 A1* 9/2013 Mayer ................ G01N 33/0031
436/147

OTHER PUBLICATIONS

Neutronics Inc., "Model N2 Operations Manual", Oct. 2006, 28 pages.
Neutronics Inc., "Model 7100P Portable Oxygen Analyzer—Trace Range Operations Manual", Jan. 2001, 58 pages.
Huntingdon Fusion Techniques, "Argweld Purgeye 300 Weld Purge Monitor", Sep. 2013, 2 pages.
Huntingdon Fusion Techniques, "Argweld Purgeye 500 Weld Purge Monitor", Sep. 2013, 2 pages.
Huntingdon Fusion Techniques, "Purgeye 600 Weld Purge Monitor", Sep. 2013, 2 pages.
Huntingdon Fusion Techniques, "Purgeye 100 Weld Purge Monitor", May 2013, 4 pages.
Prestige Industrial Pipework Equipment, "Handy Purge Pro 5", Dec. 2011, 1 page.
Prestige Industrial Pipework Equipment, "Pro Purge 1 Weld Purge Monitor", Apr. 2014, 1 page.
TVC LTD, "ALX II Portable Arc Welding Data-Logger and Monitoring System", May 2013, 2 pages.
TVC LTD, "ALX II RS Arc Welding Data-Logger and Monitoring System", Nov. 2010, 2 pages.
Advanced Instruments Inc., "GPR-1200 MS Portable ppm Oxygen Analyzer", Oct. 2009, 32 pages.

* cited by examiner

PORTABLE HAND-HELD OXYGEN MONITOR

BACKGROUND

1. Field

The present disclosure relates generally to inert gas welding. More particularly, the invention is directed to oxygen monitors for monitoring oxygen around a weld zone prior to and during an inert gas welding operation.

2. Description of the Prior Art

By way of background, inert gas welding is a species of arc welding in which the molten weld pool is shielded from atmospheric contamination and oxidation by bathing it with an inert gas, such as Argon, or a mixture of Helium and Argon. Popular examples of inert gas welding include TIG (Tungsten Inert Gas) welding and MIG (Metal Inert Gas) welding.

When welding together pipes and other enclosed structures using inert gas welding, it is important to purge the interior of the pipe or structure in the vicinity of the weld zone to prevent corrosion and the formation of oxides on the interior side of the weld pool. Purge dams are conventionally used for this purpose. For example, when butt-welding the ends of two pipe sections to form a consolidated pipe run, two purge dam structures are placed in the pipes, one in each pipe on either side of the weld zone. A purge gas can then be introduced into the area between the dams to displace the oxygen therein.

It is common to use an oxygen monitor to determine whether sufficient oxygen removal has taken place for welding operations to proceed. Historically, such oxygen monitors have been non-portable apparatus of relative large size. More recently, portable hand-held oxygen monitors have become available. Although the portability of such devices enhances ease of use, hand-held oxygen monitors typically lack one or more features, which limits their usability in the field.

It is to improvements in the design and operation of portable oxygen monitors that the present disclosure is directed.

SUMMARY

A portable hand-held oxygen monitor for monitoring oxygen in a weld zone is disclosed. The oxygen monitor includes a monitor housing having a front, a back, a top, a bottom, and two sides extending between the front and back and the top and bottom. The housing has a hand-holding portion that is sized and configured to be held in the palm of a hand of a monitor user, with the user's thumb engaging one of the sides and the user's remaining fingers engaging the other of the sides.

A user interface on the front of the housing includes an alphanumeric display and one or more user interface buttons. The alphanumeric display may comprise a backlit LCD display element. An audiovisual alarm is further provided. The audiovisual alarm includes an indicator light on the front of the housing and an audio output device within the housing, the indicator light being separate and distinct from the alphanumeric display.

The oxygen monitor further includes a power switch on the housing, a gas port on the housing operable to connect the oxygen monitor to a gas sampling probe, a digital communication port on the housing operable to connect the oxygen monitor to a separate computer via a data cable, and a charge port on the housing operable to connect the oxygen monitor to a charging device.

Within the housing is an electrochemical oxygen sensor and a pump having a pump inlet in fluid communication with the gas port and a pump outlet in fluid communication with the oxygen sensor. A microcontroller is also provided within the housing. The microcontroller includes a CPU (Central Processing Unit) coupled to a non-volatile memory that may include a program memory module and a data storage module, both of which comprise non-transitory computer-readable storage media. The microcontroller is additionally connected to the user interface, the digital communication port, the oxygen sensor, and the pump. A direct current power source within the housing is operable via the power switch and connected to provide electrical power to various oxygen monitor components, and to receive electrical power from the charge port.

The memory of the microcontroller stores program instructions that program the microcontroller CPU system to perform program operations. The program operations comprise implementing an oxygen monitoring mode responsive to activation of one or more of the user interface buttons, wherein (1) the microcontroller activates the pump to draw a gas sample from the gas port and deliver it to the oxygen sensor, (2) the oxygen sensor detects an amount of oxygen in the gas sample and outputs a corresponding voltage that is analog-to-digital converted to a digital gas sample oxygen level value, and (3) the microcontroller compares the gas sample oxygen level value to an oxygen level alarm value stored in the memory, and activates the audiovisual alarm if the gas sample oxygen level value is equal to or less than the oxygen level alarm value. Such activating includes illuminating the indicator light and generating a sound from the audio output device to alert a monitor user that is safe to weld.

In an example embodiment, the oxygen monitoring mode further comprises selectively implementing a spot monitoring mode or a continuous monitoring mode responsive to activation of one or more of the user interface buttons, the spot monitoring mode comprising obtaining a single gas sample to produce a single gas sample oxygen level value, and the continuous monitoring mode comprising obtaining gas samples periodically to produce corresponding periodic gas sample oxygen level values. The gas sample oxygen level values (regardless of mode) are output to and displayed by the alphanumeric display, and compared to the oxygen level alarm value to determine whether the audiovisual alarm should be activated.

In an example embodiment, the microcontroller repetitively activates then deactivates the indicator light and the audio output device in synchronization with each other.

In an example embodiment, the program operations further comprise implementing an alarm value set mode responsive to activation of one or more of the user interface buttons, wherein the microcontroller presents a range of suggested oxygen level alarm values to a monitor user via the user interface, and wherein the oxygen level alarm value is received as a user selection of one of the suggested oxygen level alarm values.

In an example embodiment, the program operations further comprise implementing an automatic calibration mode responsive to activation of one or more of the user interface buttons, wherein (1) the microcontroller activates the pump to draw an ambient air sample from the gas port and deliver it to the sensor, (2) the oxygen sensor detects an amount of oxygen in the ambient air sample and outputs a corresponding voltage that is analog-to-digital converted to a digital ambient oxygen level value, and (3) the microcontroller storing the ambient oxygen level value in the memory.

In an example embodiment, the microcontroller stores or computes (1) an ambient air calibration percentage value representing a known oxygen content percentage by volume for air, and (2) an ambient air calibration parts per million value representing a known oxygen content parts per million by volume for air (ppm).

In an example embodiment, the oxygen monitoring mode further comprises generating the gas sample oxygen level value as (1) an oxygen level percentage value by volume using the ambient oxygen level value and the ambient air calibration percentage value, and (2) an oxygen level ppm value using the ambient oxygen level value and the ambient air calibration ppm value.

In an example embodiment, the oxygen monitoring mode further comprises the microcontroller outputting the gas sample oxygen level value as an oxygen level percentage value and an oxygen level ppm value to the alphanumeric display, and the alphanumeric display displaying both the oxygen level percentage value and the oxygen level ppm value in alphanumeric form.

In an example embodiment, the oxygen monitoring mode further comprises the microcontroller stores logging event data in the memory, the logging event data including, for each logging event, one or more gas sample oxygen level values (e.g., stored as oxygen level percentage values) obtained during the welding operation by the oxygen monitor in association with timestamps indicating when the gas samples were obtained. The logging event data may further include weld site location information. Such information can be manually provided by a monitor user, or determined automatically by a global positioning system device inside the oxygen monitor housing. The logging event data may further include an indication of whether the audiovisual alarm was activated at the time of the logging event.

In an example embodiment, the program operations further comprise implementing a computer upload mode responsive to activation of one or more of the user interface buttons, wherein (1) the microcontroller establishes communication with a computer via the communication port, and (2) uploads the logging event data to the computer.

In an example embodiment, the portable hand-held oxygen monitor further includes a gas sampling probe connectable to the gas port, the gas sampling probe comprising a flexible gas-carrying tube having a rigid probe tip at a first end and a quick-connect fitting at a second end, the quick-connect fitting being interlockable with a counterpart quick-connect fitting mounted to the gas port, the quick-connect fittings being capable of swiveling relative to each other when connected together, thereby preventing twisting and kinking of the gas-carrying tube.

In an example embodiment, the rigid probe tip is long enough to probe to the centerline of a pipe structure to be welded, and as thin as possible while still being capable of drawing gas samples in order to minimize root gap width.

BRIEF DESCRIPTION OF THE DRAWINGS

The foregoing and other features and advantages will be apparent from the following more particular description of example embodiments, as illustrated in the accompanying Drawings, in which.

DETAILED DESCRIPTION OF EXAMPLE EMBODIMENTS

Figures 1, 2, 3:
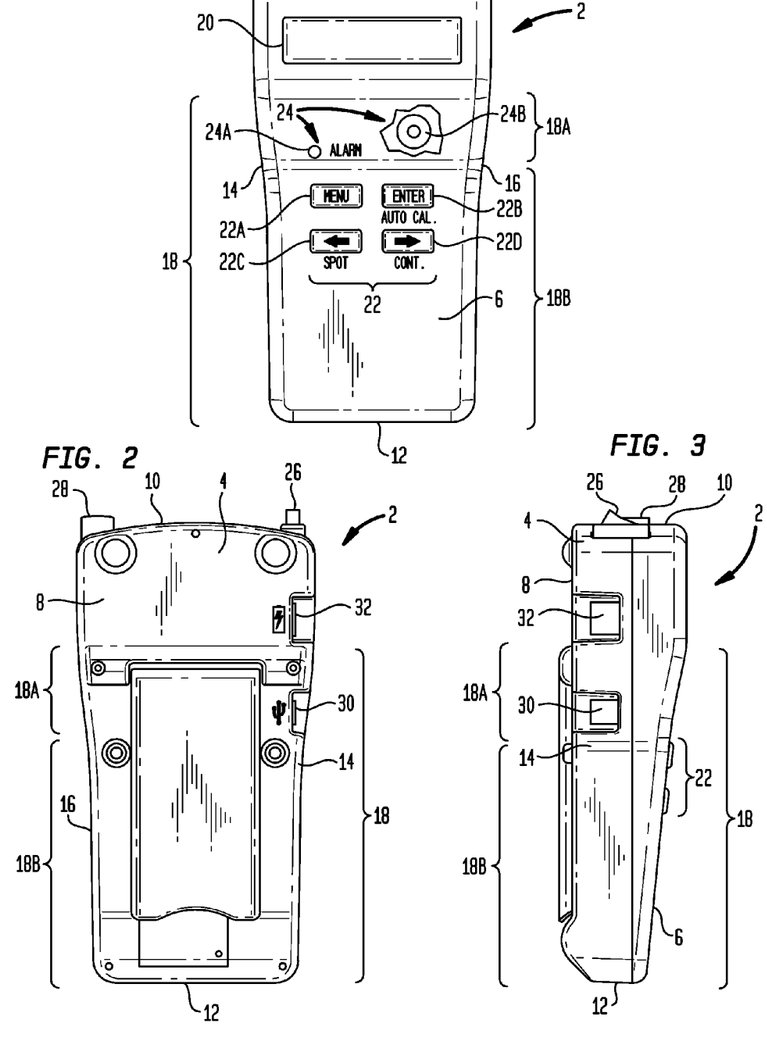
FIG. 1 is a front elevation view showing a portable hand-held oxygen monitor that may be constructed in accordance with the present disclosure, with a small section broken away to illustrate an audio output device within the monitor's housing.
FIG. 2 is a rear elevation view of the portable hand-held oxygen monitor of FIG. 1.
FIG. 3 is a side elevation view of the portable hand-held oxygen monitor of FIG. 1.

Turning now to the drawing figures, which are not necessarily to scale, like reference numbers are used to represent like elements in all of the several views. FIGS. 1-3 illustrate a handheld portable oxygen monitor 2 representing an example oxygen monitor embodiment that may be constructed in accordance with the present disclosure. The oxygen monitor 2 is particularly suited for in-the-field use, where it may be necessary to monitor oxygen in a weld zone prior to and during a welding operation performed at a remote location (e.g., as opposed to in a shop). The oxygen monitor 2 includes a monitor housing 4 having a front 6, a back 8, a top 10, a bottom 12, and two sides 14 and 16 extending between the front and back and the top and bottom. The housing 4 has a hand-holding portion 18 that is sized and configured to be held in the palm of a monitor user's hand, with the user's thumb engaging one of the sides (14 or 16) and the user's remaining fingers engaging the other of the sides (14 or 16).

A user interface on the front of the housing includes an alphanumeric display 20 and one or more user interface buttons 22. By way of example only, the alphanumeric display 20 may comprise an LCD (liquid crystal display) element, and more preferably an LED (light-emitting diode) backlit LCD element. Using a backlit LCD element allows the displayed information to be easily discerned in outdoor sunlit conditions. By way of example only, the one or more user interface buttons 22 may comprise four user interface buttons 22A, 22B, 22C and 22D are shown in FIG. 1.

The user interface button 22A is labeled "MENU." Its function is to invoke a menu mode of the oxygen monitor 2. Example menu options that may be offered in this mode are described in more detail below.

The user interface button 22B is labeled "ENTER" and sub-labeled with the abbreviated words "AUTO CAL." This button performs both menu mode and non-menu mode functions. The menu mode function is to select a menu option displayed on the alphanumeric display 18. The non-menu mode function is to initiate an automatic calibration operation. As described in more detail below, this operation involves the oxygen monitor 2 obtaining an ambient air sample and evaluating its oxygen content for calibration purposes.

The user interface button 22C is labeled with a left-pointing arrow, and is sub-labeled with the word "SPOT." This button performs performs both menu mode and non-menu mode functions. The menu mode function is to navigate through the menu mode options in a first direction. The non-menu mode function is to initiate a spot gas sampling operation. As described in more detail below, this operation involves the oxygen monitor 2 obtaining and evaluating a single gas sample.

The user interface button 22D is labeled with a right-pointing arrow, and is sub-labeled with the abbreviated word "CONT." This button performs both menu mode and non-menu mode functions. The menu mode function is to navigate through the menu mode options in a second direction. The non-menu mode function is to initiate a continuous gas sampling operation. As described in more detail below, this operation involves the oxygen monitor 2 periodically obtaining and evaluating gas samples on a continuous basis until sampling is stopped by the monitor user.

An audiovisual alarm 24 is also provided as part of the user interface. The audiovisual alarm 24 includes a small circular (or other shape) indicator light 24A on the front 6 of the housing 4, and an audio output device 24B within the housing. Advantageously, the indicator light 24A is separate and distinct from the alphanumeric display 18 (i.e., it is a separate element) in order to increase the effectiveness of the audiovisual alarm 22 and thereby simplify and enhance the monitor user's welding experience. The indicator light 24A may be positioned at any suitable location on the front 6 of the monitor housing 4. The word "ALARM" is placed next to the indicator light 24A to clearly identify it to the monitor user.

The oxygen monitor 2 further includes a power switch 26 on the housing 4, a gas port 28 on the housing operable to connect the oxygen monitor 2 to a gas sampling probe 29 (shown in FIG. 7), a digital communication port 30 on the housing operable to connect the oxygen monitor to a separate computer (not shown) via a data cable (not shown), and a charge port 32 on the housing operable to connect the oxygen monitor 2 to a charging device (not shown).

If desired, the sides 14 and 16 of the housing 4 may be contoured such that the two sides are varyingly tapered along the length of the hand-holding portion 18. For example, as shown in FIGS. 1 and 2, the sides 14 and 16 may have a first relatively steep taper over a relatively short upper segment 18A of the hand-holding portion 18, and a second relatively shallow taper over a relatively long lower segment 18B of the hand-holding portion. With this configuration, the sides 14 and 16 of the housing over the length of the hand-holding portion 18 will tend to match the naturally tapering space between the human thumb and remaining figures of the monitor user's hand as it grasps the housing 4, thereby improving ergonomic comfort.

If desired, the front 6 of the housing 4 may also be contoured such that it is varyingly tapered along the length of the hand-holding portion 18. For example, as shown in FIG. 3, the front 6 may have a first relatively steep taper over the relatively short upper segment 18A of the hand-holding portion 18, and a second relatively shallow taper over the relatively long lower segment 18B of the hand-holding portion. With this configuration, the indicator light 24A of the audiovisual alarm 24, which is located on the relatively steeply tapered upper segment 18A, will be more prominently viewable and differentiable from the alphanumeric display 20, which is located above the hand-holding portion 18 of the housing 4. The user interface buttons 22 are located on the relatively shallowly tapered lower segment 18B. The shallow taper enhances the ergonomic presentation of these buttons to the monitor user.

Although varyingly tapered, the hand-holding portion 18 of the housing 4 will inherently have an average thickness dimension and an average width dimension. The average thickness dimension represents the average distance between the front 6 and back 8 of the housing 4 over the length of the hand-holding portion 18. The average width dimension represents the average distance between the two sides 14 and 16 of the housing 4 over the length of the hand-holding portion 18. In an example embodiment, the average thickness dimension is preferably less than or equal to the average width dimension to provide satisfactory ergonomic comfort. By way of example, the average thickness dimension may be approximately 1.5-2.5 inches, and the average width dimension may be approximately 2.5-3.5 inches.

Figure 4:
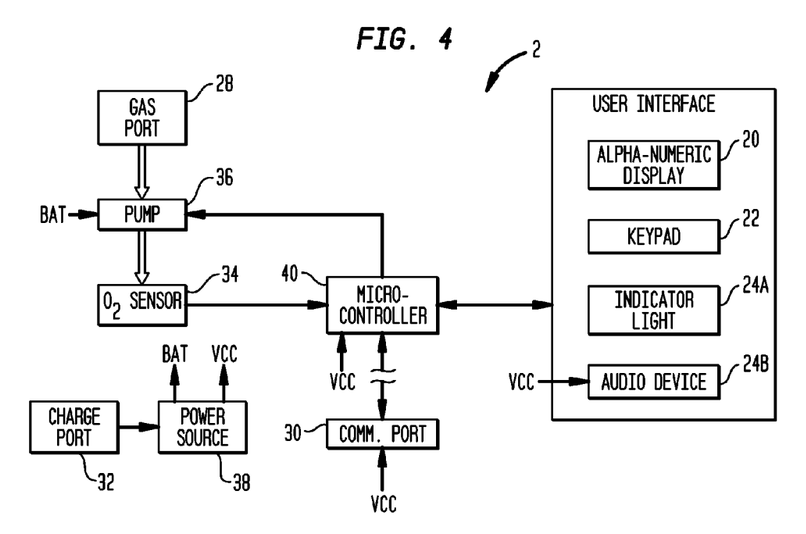
FIG. 4 is a functional block diagram showing example components of the portable hand-held oxygen monitor of FIG. 1.
Figure 5:
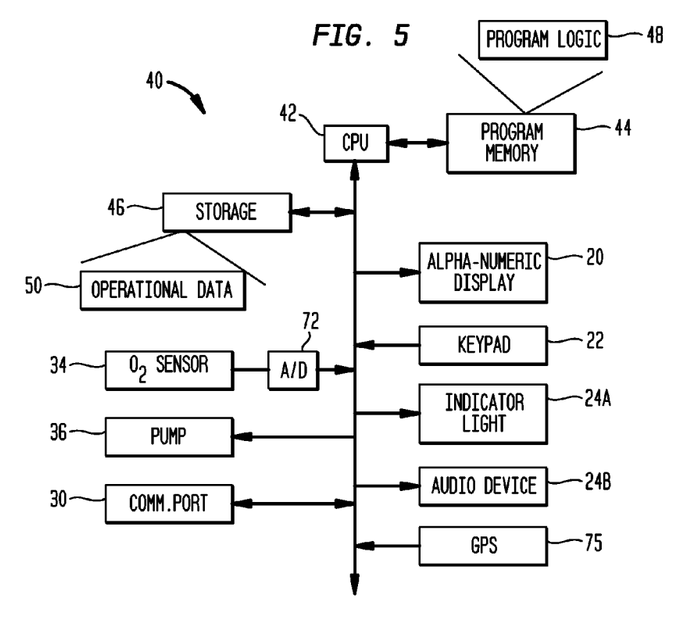
FIG. 5 is a functional block diagram showing an example microcontroller and its connections to other components of the portable hand-held oxygen monitor of FIG. 1.

With additional reference now to FIG. 4, within the housing 4 is an electrochemical oxygen sensor 34 and a pump 36 having a pump inlet in fluid communication with the gas port 28 and a pump outlet in fluid communication with the oxygen sensor. A direct current power source 38 is also provided within the housing 4, as is a microcontroller 40. As shown in FIG. 5, the microcontroller 40 includes a CPU (Central Processing Unit) 42 operably coupled to a non-volatile program memory module 44 (such as a flash program memory) via a memory bus, and to a non-volatile storage module 46 (such as a standard EEPROM) via a main bus. The program memory module 44 and the storage module 46 comprise non-transitory computer-readable storage media, and each represents a type of microcontroller "memory." The program memory module is used to store microcontroller program instructions and temporary (e.g., stack) data, identified in FIG. 5 as program logic 48. The storage module 46 is used to store permanent data, including data generated during oxygen monitor operations, identified in FIG. 5 as operational data 50. The microcontroller 40 is further operably coupled to the user interface components 20, 22, 24A and 24B, the digital communication port 30 (via a communications protocol controller (not shown)), the oxygen sensor 34, the pump 36 and the direct current power source 38. The direct current power source 38 is operable via the power switch 26 and connected to provide electrical power to various monitor components, and to receive electrical power from the charge port 32. In an example embodiment, the power source 38 may be implemented as a rechargeable battery.

Figure 6:
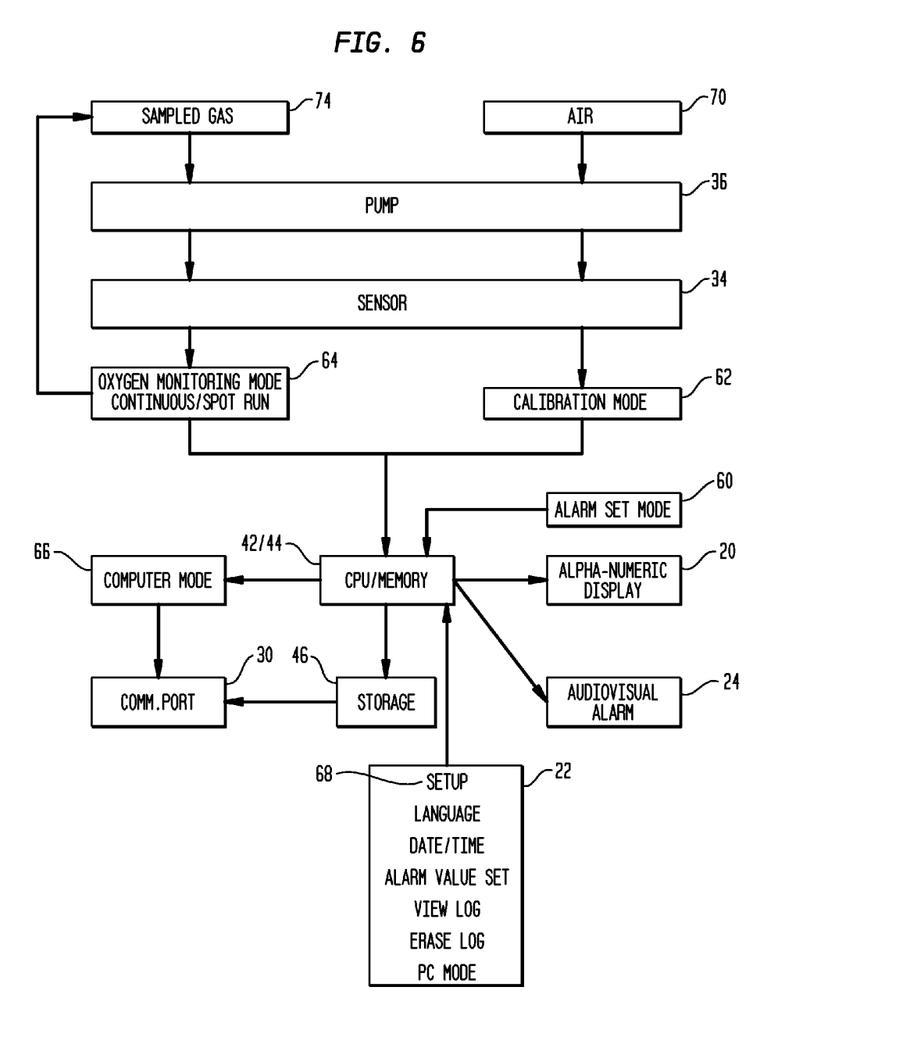
FIG. 6 is a functional block diagram showing example functions (and components) of the portable hand-held oxygen monitor of FIG. 1.

The programming instructions comprising the program logic 48 are used to program the microcontroller's CPU 42 to perform various functions and operations. As shown in FIG. 6, these functions and operations may include an alarm value set mode 60, an automatic calibration mode 62, an oxygen monitoring mode 64, and a computer mode 66. Each of these operational modes is implemented by the microcontroller 40 in response to activation of one or more of the user interface buttons 22. Example embodiments of these operational modes are described in more detail hereinafter.

Two of the operational modes, namely, the alarm value set mode 60 and the computer mode 66, are invoked via the MENU button 22A. Thus, it is appropriate to briefly discuss the various menu options that this button may be configured to provide. In the embodiment of FIGS. 1-6, the MENU button 22A is used to display a SETUP menu 68 on the alphanumeric display 20. Only one menu option is displayed at a time. Desired options are reached using the buttons 22C and 22D to scroll through the selections, and then pressing the ENTER button 22B to select the option of interest. The first three options are a LANGUAGE setup option for selecting a desired display language, a DATE/TIME setup option for inputting the date and time of a particular welding job, and an ALARM VALUE SET option for invoking the alarm value set mode 60. These first three options are for use prior to the oxygen monitor 2 being operated for purging. Note that in addition to allowing a monitor user to store date and time information for a particular welding job, one or more additional SETUP menu options could be added to allow a monitor user to store additional job information, such as weld site location in case the welding log data stored by the oxygen monitor (see below) ever needs to be associated with a particular welding location on a pipeline or other structure (e.g. for forensic purposes). The second three options provided by the SETUP menu 68 are a VIEW LOG option for viewing log data concerning a welding job, an ERASE LOG option for erasing the log data, and a PC MODE option for invoking the computer mode 66 in order to upload the log data to a separate computer.

The alarm value set mode 62 allows a monitor user to specify an oxygen level that will trigger an alarm output from the audiovisual alarm 24 during the oxygen monitoring mode 64. As mentioned above, the program operations comprising the alarm value set mode 62 are invoked using the MENU button 22A. This displays the SETUP menu 68 in the alphanumeric display 20. The monitor user presses either of buttons 22C or 22D to scroll through the menu selections until the ALARM VALUE SET option is reached, and then presses the ENTER button 22B. When the ALARM VALUE SET option is invoked, the microcontroller 40 presents a range of suggested oxygen level alarm values for selection by the monitor user via the user interface 22. By way of example, the oxygen level alarm values may be presented as a list that the monitor user can step through in a forward direction by pressing the arrow button 22D or in a reverse direction by pressing the arrow button 22C. When the desired oxygen level alarm value is reached, the monitor user presses the ENTER button 22B. This will cause the microcontroller 40 to receive the oxygen level alarm value as a user selection, and store it the microcontroller's memory, namely, as part of the operational data 50 in the storage module 46. As a further option, the oxygen monitor 2 could be configured so that the ALARM VALUE SET menu option allows a monitor user to disable the audiovisual alarm 24.

The program operations comprising the automatic calibration mode 62 are implemented (when the oxygen monitor is not in menu mode) in response to the monitor user pressing the AUTO CAL. button 22A. As shown in FIG. 6, when the automatic calibration mode 52 is invoked, the microcontroller 40 activates the pump 36 to draw an ambient air sample 70 from the probe attached to the gas port 28, and deliver the sample to the oxygen sensor 34. The oxygen sensor 34 detects the amount of oxygen in the ambient air sample 70, and outputs a corresponding analog voltage. The oxygen sensor's analog voltage output is input to an A/D (Analog/Digital) converter 72 in the microcontroller 40 (see FIG. 5), which converts the analog voltage to a digital ambient oxygen level value. The ambient oxygen level value is stored as part of the operational data 50 in the microcontroller's memory, namely, in the storage module 46.

In an example embodiment, the storage module 46 also stores an ambient air calibration percentage value representing a known oxygen content percentage for air. For example, at sea level, the oxygen content of air, by volume, is 20.946%. This default percentage value may be placed in the storage module 46 as a factory setting of the oxygen monitor 2. It need not be set by the monitor user. By knowing both the oxygen content of air as a percentage value and the ambient oxygen level value determined during automatic calibration, the microcontroller 40 can determine the oxygen content of a gas sample obtained during welding and display it as a percentage value. This is described in more detail below in the discussion of the oxygen monitoring mode 64. As also described below, the oxygen content of a gas sample obtained during welding can be additionally displayed in parts per million by volume (ppm). This may be done using a stored ambient air calibration ppm value representing a known oxygen ppm for air. Or, the ambient air calibration ppm value may be easily computed from the ambient air calibration percentage value. For example, given that the oxygen content in air is 20.946% by volume, its ppm would be 0.20946×1 million=209,460 ppm. It would also be possible to store the ambient air calibration ppm value and compute the ambient air calibration percentage value therefrom. Once automatic calibration is done, the monitor user can operate the oxygen monitor 2 to measure the oxygen level in a welding purge zone prior to and during a welding operation.

The program operations comprising the oxygen monitoring mode 64 are implemented (when the oxygen monitor is not in menu mode) in response to the monitor user pressing either the SPOT button 22C or the CONT. button 22D. The SPOT button 22C invokes spot monitoring to obtain a single oxygen reading whereas the CONT. button 22D invokes continuous monitoring to obtain plural periodic oxygen readings. As shown in FIG. 6, when either button is pressed, the microcontroller 40 activates the pump 36 to draw a sample of the unknown gas 74 from the probe attached to the gas port, and deliver it to the oxygen sensor 34. The oxygen sensor 34 detects the amount of oxygen in the gas sample 74 and outputs a corresponding analog voltage that is converted by the A/D converter to a digital gas sample oxygen level value. The microcontroller 40 then compares the gas sample oxygen level value to the oxygen level alarm value previously stored in the memory, and activates the audiovisual alarm 24 if the gas sample oxygen level value is equal to or less than the oxygen level alarm value. This activating includes illuminating the indicator light and generating a sound from the audio output device to alert a monitor user that is safe to weld. Preferably, the microcontroller repetitively activates then deactivates the indicator light and the audio output device in synchronization with each other in order to increase the effectiveness of the alert by making it more distinct.

In an example embodiment, the oxygen monitoring mode 64 further includes the microcontroller 40 outputting the gas sample oxygen level value to the alphanumeric display 20, and the alphanumeric display displaying the value in alphanumeric form. Preferably, the gas sample oxygen level value is displayed as both an oxygen level percentage value (by volume) and an oxygen level ppm value. This is advantageous because some monitor users are used to working with oxygen percentage values while others are used to working with ppm values. A menu option could also be provided for selectively displaying oxygen percentage values or ppm values.

Determining an oxygen percentage value can be handled using the gas sample oxygen level value in conjunction with the ambient oxygen level value and the ambient air calibration percentage value described above. In particular, the oxygen percentage of the gas sample 74 can be determined by Equation (1) below:

$$\text{gas sample oxygen level percentage value} = (\text{ambient air calibration percentage value}) \times (\text{gas sample oxygen level value/ambient oxygen level value}). \quad \text{Equation (1):}$$

Similarly, determining an oxygen ppm value can be handled using the gas sample oxygen level value in conjunction with the ambient oxygen level value and the ambient air calibration ppm value described above (which may be separately stored or derived on the fly from the ambient air calibration value. In particular, the oxygen level ppm of the gas sample 74 can be determined by Equation (2) below:

$$\text{gas sample oxygen level ppm value} = (\text{ambient air calibration ppm value}) \times (\text{gas sample oxygen level value/ambient oxygen level value}). \quad \text{Equation (2):}$$

If the oxygen monitoring mode 64 is invoked by the SPOT button 22C to obtain a spot reading, the foregoing operations happen only once. If the oxygen monitoring mode 64 is invoked by the CONT. button 22D to obtain continuous readings, the foregoing operations are repeated periodically at predetermined intervals (e.g., every second) on a continuous basis, until the monitor user discontinues oxygen monitoring by pressing the CONT. button a second time.

In an example embodiment, the oxygen monitoring mode 64 includes data logging in which the microcontroller stores logging event data as part of the operational data 50 in the microcontroller's memory, namely, in the storage module 46. Logging is preferably implemented automatically, with user control being limited to viewing log data via the VIEW LOG menu option or deleting it via the ERASE LOG menu option. Alternatively, the oxygen monitor 2 could be configured to allow the monitor user to enable or disable logging.

The logging event data may include, for each logging event, one or more gas sample oxygen level values obtained during the welding operation by the oxygen monitor 2 are stored in association with timestamps indicating when the gas samples were obtained. The oxygen level values may be stored in raw form, as oxygen level percentage values, as oxygen level ppm values, or any combination of the above. The logging event data may also indicate whether the audiovisual alarm 24 was activated at the time of the logging event. For spot oxygen monitoring, there will be a single logging event. For continuous oxygen monitoring, there will be several logging events. By way of example, a logging event could be performed for every "n" gas sample readings, where "n" is selected based on a desired logging event frequency taking into the account the limits on storage space available in the storage module 46. Thus, if gas sample readings are taken once per second, a logging event could be performed every 15 readings, representing a 15 second time span between logging events. The timetamp information stored in a logging event could be the DATE/TIME information entered via the SETUP menu 68. Additionally, the microcontroller 40 could generate individual timestamps each time a gas sample 74 is obtained. Other information stored via the SETUP menu in connection with a particular welding job could also be logged. By way of example, this could include weld location information, such as a location on a pipeline or other welded structure where a weld was made and the logging data was generated. One advantage of capturing such location information would be for forensic purposes in the event of a subsequent weld failure. Although not shown, an embodiment of the oxygen monitor 2 could include a locating device, such as a GPS (global positioning system) unit 75 (see FIG. 5), that can automatically generate the monitor location information for storage as part of the operational data 50 in the microcontroller's memory, namely, in the storage module 46. The automated location information could be stored as part of the logging data.

As mentioned above, the program operations comprising the computer mode 66 are invoked using the MENU button 22A. This displays the SETUP menu 68 in the alphanumeric display 20. The monitor user presses either of buttons 22C or 22D to scroll through the menu selections until the PC MODE option is reached, and then presses the ENTER button 22B. When the PC MODE option is invoked, the microcontroller 40 presents establishes communication with a separate computer connected to the communication port 30 via a cable, and (2) uploads the logging event data from the microcontroller memory, namely the storage module 46, to the computer. If desired, the oxygen monitor 2 could also be provisioned with an RF transceiver for wireless communication (e.g., using a WIFI or Bluetooth protocol).

Figures 7, 7A:
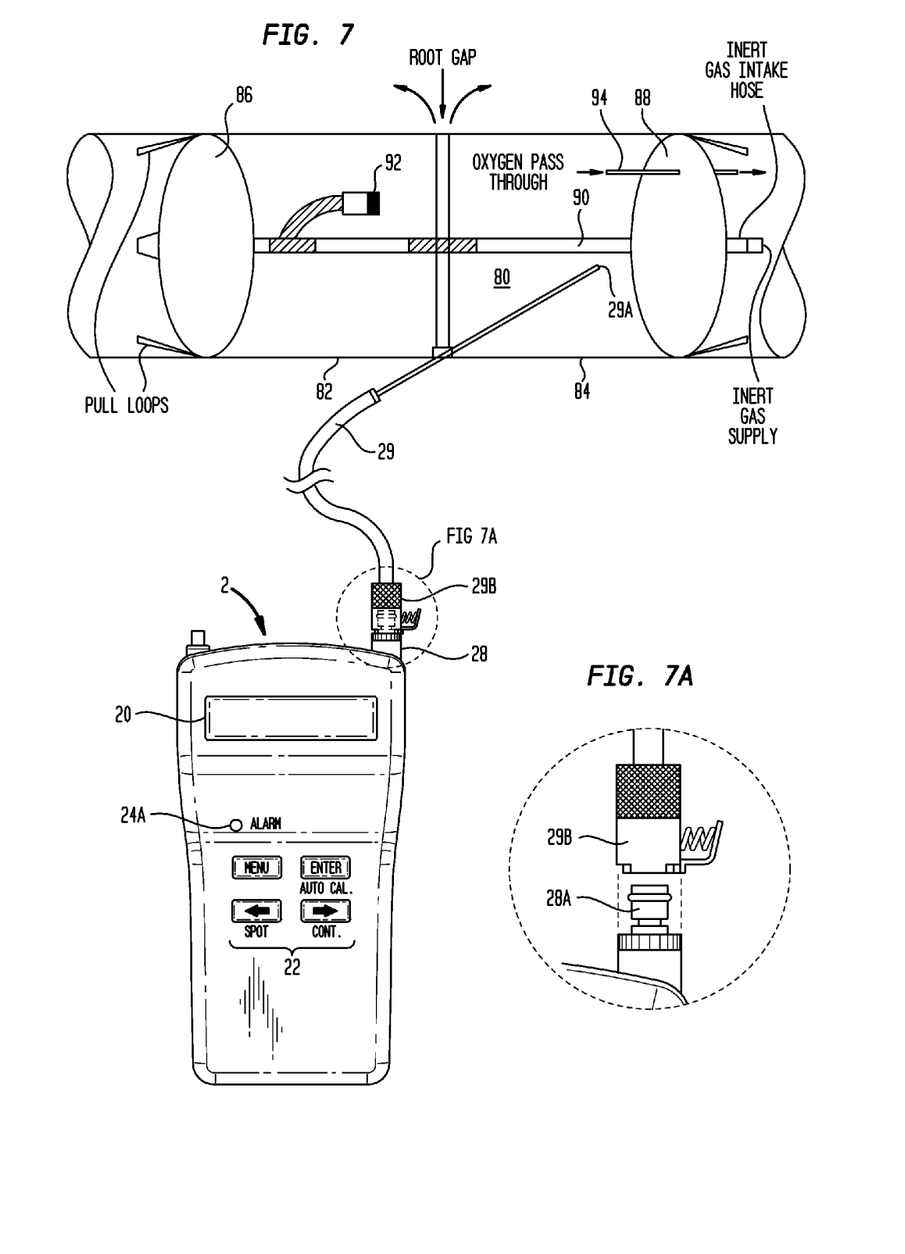
FIG. 7 is a diagrammatic view showing the portable hand-held oxygen monitor of FIG. 1 being used to monitor oxygen in a weld zone during a pipe-welding purge operation.
FIG. 7A is an inset view from FIG. 7 showing a quick-connect coupling between a gas port of the portable hand-held oxygen of FIG. 1 and a gas-sampling probe.

Turning now to FIG. 7, the portable oxygen monitor 2 is shown as it monitors oxygen in a pipeline weld zone 80 during a weld zone purging operation. In FIG. 7, a pair of pipes 82/84 are to be butt-welded together at a welding root gap. A purge dam apparatus installed within the pipes has first and second pipe blocking members 86 and 88 that, for purposes of example only, may be implemented as inflatable purge bladders. The purge bladders 86 and 88 are joined together by an intermediate bridge conduit 90. FIG. 7 shows the purge dam apparatus after the purge bladders 86 and 88 have been inflated with an inert gas from an inert gas supply (not shown). The inert gas is fed from the inert gas supply through an inert gas intake hose connected to a port on the right-hand purge bladder 88. The inert gas inflates both purge bladders 86/88, and also flows into the weld zone 80 via a purge gas outlet port 92 connected to the bridge conduit 90. The enclosed space between the purge bladders represents the weld zone 80, which is purged of air by the purge gas following the introduction thereof through the purge gas outlet port 92. Oxygen displaced by the incoming purge gas exits the weld zone 80 via the root gap, and also through a vent port 94 extending through the right-hand purge bladder 88.

As can be seen, the oxygen monitor 2 is operable to obtain oxygen readings from the weld zone 80 using the detachable probe 29. A rigid probe tip 29A at the inlet end of the probe 29 is inserted into the root gap so that it can draw gas samples from the weld zone 90. The probe tip 29A can be made of steel or other material that can withstand the heat from the welding operation. Advantageously, the probe tip 29A is long so that it can collect gas samples from deep in the weld zone 80. Preferably, the probe tip 29A is at least approximately 100 mm long so that it can will reach the centerline of a pipe having a diameter of 200 mm. More preferably, the probe tip 29A will be longer so that it can probe the side regions of the weld zone 80, as shown in FIG. 7. In an example embodiment, the probe tip 29A is at least approximately 160 mm in length. The probe tip 29A is also as thin as possible while still being capable of drawing gas samples in order to minimize root gap width. Preferably, the outside diameter of the probe tip 29A will not exceed approximately 5 mm. In an example embodiment, the probe tip 29A has an outside diameter of not more than approximately 2 mm, with an inside diameter of approximately 1 mm. The base end of the probe tip has an enlarged fitting that mounts to one end of a flexible tube portion of the probe 29.

The outlet end of the probe 29 mounts a female quick-connect fitting 29B that is connected to a counterpart male quick-connect fitting 28A mounted on the gas port 28 on the oxygen monitor 2. The female quick-connect fitting 29B is provided with a spring-loaded disconnect push button clasp that lockingly engages a channel on the male quick-connect fitting 28A, such that the quick-connect fittings are hand-operable. A resilient O-ring is provided on the male quick-connect fitting 28A to ensure a high-quality pressure seal. The above-described style of hand-operable quick-connect coupling is conventionally used with low pressure tubing. Other types of hand-operable quick-connect couplings may also be used in lieu of the illustrated components.

The quick-connect fittings 28A and 29B interlock to form a gas-tight connection between the oxygen monitor 2 and the probe 29. This interlocked coupling arrangement prevents gas leakage, which has been known to occur in prior art oxygen monitors in which a threaded connection is used for the probe. In such prior art oxygen monitors, the monitor user may fail to fully thread the probe onto the monitor. Also, rotation of the oxygen monitor or the probe creates torque that can loosen the threaded connection, or twist and kink the probe's flexible tube, which can lead to false oxygen level readings. In the disclosed oxygen monitor 2, the quick-connect fitting 29B is free to swivel when interlocked with the quick-connect fitting 28A, thereby eliminating torque, and twisting and kinking of the probe tube.

One or more oxygen samples may be obtained prior to welding as oxygen is displaced from the weld zone 80 by the inert gas during purging. Once the oxygen level in the weld zone 80 has dropped to the oxygen level alarm value stored by the oxygen monitor 2, the audiovisual alarm 24 will activate, alerting the monitor user that welding may proceed.

Advantageously, the monitor user does not have to watch the alphanumeric display 20 to determine when the desired oxygen level has been reached. The monitor user may simply listen for the audio device 24B to trigger, then optionally glance at the indicator light 24A if the user wishes to verify that it too has been activated. If additional assurance is needed, the monitor use can also check the alphanumeric display 20 to confirm the actual oxygen level percentage value for the weld zone 80. Prior to the time that the audiovisual alarm 24 activates, the monitor user may perform other useful functions, such as preparing the welding equipment for the welding operation. The monitor user does not have to be distracted by periodically checking the alphanumeric display 20. Once welding begins, the oxygen monitor 2 may be used to draw additional gas samples, for as long as the probe 29 can remain in place, thereby verifying that the weld zone 80 is being maintained at a suitably low oxygen level. Again, the audiovisual indicator 24 will provide the requisite information without the monitor user having to be distracted from the welding task by watching the alphanumeric display 20. As long as the audiovisual indicator 24 continues to output an audiovisual alarm, the monitor user will know it is safe to continue welding.

Accordingly, a portable hand-held oxygen monitor for monitoring oxygen in a weld zone has been disclosed. Although various embodiments have been shown and described, it should be apparent that many variations and alternative embodiments could be implemented in accordance with the invention. It is understood, therefore, that the invention is not to be in any way limited except in accordance with the spirit of the appended claims and their equivalents.

What is claimed is:
1. A portable hand-held oxygen monitor for monitoring oxygen in a weld zone, comprising:
 a monitor housing, said housing having a front, a back, a top, a bottom, and two sides extending between said front and back and said top and bottom;
 said housing having a hand-holding portion that is sized and configured to be held in the palm of a hand of a monitor user, with the user's thumb engaging by directly contacting one of said sides and the user's remaining fingers engaging by directly contacting the other of said sides;
 said hand-holding portion having an average thickness dimension representing a separation distance between said front and back of said housing of approximately 1.5-2.5 inches, and an average width dimension representing a separation distance between said sides of said housing of approximately 2.5-3.5 inches;
 a user interface on said front of said housing, said user interface including an alphanumeric display operable to display a gas sample oxygen level value, and one or more user interface buttons;
 an audiovisual alarm comprising a non-alphanumeric indicator light on said front of said housing and an audio output device within said housing, said indicator light being separate and distinct from said alphanumeric display;
 a power switch on said housing;
 a quick-connect gas port on said housing operable to connect said oxygen monitor to a gas sampling probe;
 a digital communication port on said housing operable to connect said oxygen monitor to a computer via a data cable;
 a battery charge port on said housing operable to connect said oxygen monitor to a battery charging device;
 an electrochemical oxygen sensor within said housing;
 a pump within said housing having a pump inlet in fluid communication with said gas port and a pump outlet in fluid communication with said oxygen sensor;
 a microcontroller within said housing, said microcontroller including a microcontroller coupled to memory comprising a non-transitory computer-readable storage medium, said microcontroller being connected to said user interface, said audiovisual alarm, said digital communication port, said oxygen sensor, and said pump;
 a direct current battery power source within said housing operable via said power switch and connected to provide electrical power to said monitor, and to receive electrical power from said battery charge port;
 said memory of said microcontroller storing program instructions that program said microcontroller to perform program operations, said program operations comprising:
 implementing an oxygen monitoring mode responsive to activation of one or more of said user interface buttons, wherein (1) said microcontroller activates said pump to draw a gas sample from said gas port and deliver it to said oxygen sensor, (2) said oxygen sensor detects an amount of oxygen in said gas sample and outputs a corresponding voltage that is processed into a digital gas sample oxygen level value, (3) said microcontroller outputting said gas sample oxygen level value on said alphanumeric display, (4) said microcontroller comparing said gas sample oxygen level value to an oxygen level alarm value stored in said memory, and activating said audiovisual alarm if said gas sample oxygen level value is less than said oxygen level alarm value, said activating comprising illuminating said indicator light and generating a sound from said audio output device to alert a monitor user that is safe to weld.

2. The portable hand-held oxygen monitor of claim 1, wherein said oxygen monitoring mode further comprises selectively implementing a spot monitoring mode or a continuous monitoring mode responsive to activation of one or more of said user interface buttons, said spot monitoring mode comprising obtaining a single gas sample to produce a single gas sample oxygen level value in response to activation of a spot monitoring mode user interface button, said spot monitoring mode obtaining and evaluating not more than said single gas sample for any given activation of said spot monitoring mode user interface button, and said continuous monitoring mode comprising obtaining gas samples periodically to produce corresponding periodic gas sample oxygen level values in response to activation of a continuous monitoring mode button, said continuous monitoring mode obtaining and evaluating said periodic gas samples on a continuous basis until sampling is stopped by a user.

3. The portable hand-held oxygen monitor of claim 2, wherein said activating said audiovisual alarm comprises said microcontroller repetitively activating then deactivating said indicator light and said audio output device in synchronization with each other.

4. The portable hand-held oxygen monitor of claim 1, wherein said program operations further comprise:
implementing an alarm value set mode responsive to activation of one or more of said user interface buttons, wherein said microcontroller presents a range of microcontroller-suggested numeric oxygen level alarm values to a monitor user via said user interface, and wherein said oxygen level alarm value is a number received as a user selection of one of said suggested numeric oxygen level alarm values, said suggested numeric oxygen level alarm values being presented as a step-through list of said numeric oxygen level alarm values that a user can step through until a desired oxygen level alarm value is reached.

5. The portable hand-held oxygen monitor of claim 4, wherein said program operations further comprise:
implementing an automatic calibration mode responsive to activation of one or more of said user interface buttons, wherein (1) said microcontroller activates said pump to draw an ambient air sample from said gas port and deliver it to said sensor, (2) said oxygen sensor detects an amount of oxygen in said ambient air sample and outputs a corresponding voltage that is processed into a digital ambient oxygen level value, and (3) said microcontroller storing said ambient oxygen level value in said memory.

6. The portable hand-held oxygen monitor of claim 5, wherein said microcontroller stores or computes (1) an ambient air calibration percentage value representing a known oxygen content percentage by volume for air, and (2) an ambient air calibration parts per million value representing a known oxygen content parts per million by volume for air (ppm).

7. The portable hand-held oxygen monitor of claim 6, wherein said oxygen monitoring mode further comprises generating said gas sample oxygen level value as (1) an oxygen level percentage by volume value using said ambient oxygen level value and said ambient air calibration percentage value, and (2) an oxygen level ppm value using said ambient oxygen level value and said ambient air calibration ppm value.

8. The portable hand-held oxygen monitor of claim 7, wherein said oxygen monitoring mode further comprises said microcontroller outputting said gas sample oxygen level value as said oxygen level percentage value and said oxygen level ppm value to said alphanumeric display, and said alphanumeric display displaying one or both of said oxygen level percentage value and said oxygen level ppm value in alphanumeric form.

9. The portable hand-held oxygen monitor of claim 1, wherein said oxygen monitoring mode further comprises said microcontroller storing logging event data in said memory, said logging event data including, for each logging event, one or more gas sample oxygen level values obtained during said welding operation by said oxygen monitor in association with timestamps indicating when said gas samples were obtained, said logging event data further including welding job information input via said user interface.

10. The portable hand-held oxygen monitor of claim 9, wherein said logging event data includes weld site location information.

11. The portable hand-held oxygen monitor of claim 10, wherein said weld site location information determined automatically by a global positioning system device inside said oxygen monitor housing.

12. The portable hand-held oxygen monitor of claim 9, wherein said logging event data includes an indication of whether said audiovisual alarm was activated at the time of the logging event.

13. The portable hand-held oxygen monitor of claim 9, wherein said program operations further comprise:
implementing a computer upload mode responsive to activation of one or more of said user interface buttons, wherein (1) said microcontroller establishes communication with a computer via said communication port, and (2) uploads said logging event data to said computer.

14. The portable hand-held oxygen monitor of claim 1, wherein said alphanumeric display comprises a backlit LCD display element.

15. The portable hand-held oxygen monitor of claim 1, further including a gas sampling probe connectable to said gas port, said gas sampling probe comprising a flexible gas-carrying tube having a rigid probe tip at a first end and a quick-connect fitting at a second end, said quick-connect fitting being interlockable with a counterpart quick-connect fitting mounted to said gas port, said quick-connect fittings being capable of swiveling relative to each other when connected together, thereby preventing twisting and kinking of said gas-carrying tube.

16. The portable hand-held oxygen monitor of claim 15, wherein said rigid probe tip is configured to probe to the centerline of a pipe structure to be welded.

17. The portable hand-held oxygen monitor of claim 16, wherein said rigid probe tip is at least approximately 100 mm in length and has an outside diameter of not more than approximately 5 mm.

18. The portable hand-held oxygen monitor of claim 17, wherein said rigid probe tip is at least approximately 160 mm in length and has an outside diameter of not more than approximately 2 mm, with an inside diameter of approximately 1 mm.

19. A portable hand-held oxygen monitor for monitoring oxygen in a weld zone, comprising:
a monitor housing, said housing having a front, a back, a top, a bottom, and two sides extending between said front and back and said top and bottom;

said housing having a hand-holding portion that is sized and configured to be held in the palm of a hand of a monitor user, with the user's thumb engaging by directly contacting one of said sides and the user's remaining fingers engaging by directly contacting the other of said sides;

said hand-holding portion having an average thickness dimension representing a separation distance between said front and back of said housing of approximately 1.5-2.5 inches, and an average width dimension representing a separation distance between said sides of said housing of approximately 2.5-3.5 inches;

a user interface on said front of said housing, said user interface including an alphanumeric display operable to display a gas sample oxygen level value, and one or more user interface buttons;

an audiovisual alarm comprising non-alpha-numeric indicator light on said front of said housing and an audio output device within said housing, said indicator light being separate and distinct from said alphanumeric display;

a power switch on said housing;

a quick-connect gas port on said housing operable to connect said oxygen monitor to a gas sampling probe;

a digital communication port on said housing operable to connect said oxygen monitor to a computer via a data cable;

a battery charge port on said housing operable to connect said oxygen monitor to a battery charging device;

an electrochemical oxygen sensor within said housing;

a pump within said housing having a pump inlet in fluid communication with said gas port and a pump outlet in fluid communication with said oxygen sensor;

a microcontroller within said housing, said microcontroller including a microcontroller coupled to memory comprising a non-transitory computer-readable storage medium, said microcontroller being connected to said user interface, said audiovisual alarm, said digital communication port, said oxygen sensor, and said pump;

a direct current battery power source within said housing operable via said power switch and connected to provide electrical power to said monitor, and to receive electrical power from said battery charge port;

said memory of said microcontroller storing program instructions that program said microcontroller to perform program operations;

said program operations comprising implementing an oxygen monitoring mode responsive to activation of one or more of said user interface buttons, wherein (1) said microcontroller activates said pump to draw a gas sample from said gas port and deliver it to said oxygen sensor, (2) said oxygen sensor detects an amount of oxygen in said gas sample and outputs a corresponding voltage that is processed into a digital gas sample oxygen level value, (3) said microcontroller outputting said gas sample oxygen level value on said alphanumeric display, (4) said microcontroller comparing said gas sample oxygen level value to an oxygen level alarm value stored in said memory, and activating said audiovisual alarm if said gas sample oxygen level value is less than said oxygen level alarm value, said activating comprising illuminating said indicator light and generating a sound from said audio output device to alert a monitor user that is safe to weld;

said oxygen monitoring mode further comprising selectively implementing a spot monitoring mode or a continuous monitoring mode responsive to activation of one or more of said user interface buttons, said spot monitoring mode comprising obtaining a single gas sample to produce a single gas sample oxygen level value in response to activation of a spot monitoring mode user interface button, said spot monitoring mode obtaining and evaluating not more than said single gas sample for any given activation of said spot monitoring mode user interface button, and said continuous monitoring mode comprising obtaining gas samples periodically to produce corresponding periodic gas sample oxygen level values in response to activation of a continuous monitoring mode button, said continuous monitoring mode obtaining and evaluating said periodic gas samples on a continuous basis until sampling is stopped by a user;

said activating said audiovisual alarm comprising said microcontroller repetitively activating then deactivating said indicator light and said audio output device in synchronization with each other;

said program operations further comprising implementing an alarm value set mode responsive to activation of one or more of said user interface buttons, wherein said microcontroller presents a range of microcontroller-suggested numeric oxygen level alarm values to a monitor user via said user interface, and wherein said oxygen level alarm value is a number received and stored as a user selection of one of said suggested numeric oxygen level alarm values, said suggested numeric oxygen level alarm values being presented as a step-through list of said numeric oxygen level alarm values that a user can step through until a desired oxygen level alarm value is reached;

said program operations further comprising implementing an automatic calibration mode responsive to activation of one or more of said user interface buttons, wherein (1) said microcontroller activates said pump to draw an ambient air sample from said gas port and deliver it to said sensor, (2) said oxygen sensor detects an amount of oxygen in said ambient air sample and outputs a corresponding voltage that is processed into a digital ambient oxygen level value, and (3) said microcontroller storing said ambient oxygen level value in said memory;

said microcontroller storing or computing (1) an ambient air calibration percentage value representing a known oxygen content percentage by volume for air, and (2) an ambient air calibration parts per million value representing a known oxygen content parts per million by volume for air (ppm);

said oxygen monitoring mode further comprising generating said gas sample oxygen level value as (1) an oxygen level percentage by volume value using said ambient oxygen level value and said ambient air calibration percentage value, and (2) an oxygen level ppm value using said ambient oxygen level value and said ambient air calibration ppm value;

said oxygen monitoring mode further comprising said microcontroller outputting said gas sample oxygen level value as said oxygen level percentage value and said oxygen level ppm value to said alphanumeric display, and said alphanumeric display displaying one or both of said oxygen level percentage value and said oxygen level ppm value in alphanumeric form;

said oxygen monitoring mode further comprising said microcontroller storing logging event data in said memory, said logging event data including, for each logging event, one or more gas sample oxygen level values obtained during said welding operation by said oxygen monitor in association with timestamps indicating when said gas samples were obtained, said logging event further including welding job information input via said user interface;

said logging event data including weld site location information;

said weld site location information being determined automatically by a global positioning system inside said oxygen monitor housing;

said logging event data including an indication of whether said audiovisual alarm was activated at the time of the logging event;

said program operations further comprising implementing a computer upload mode responsive to activation of one or more of said user interface buttons, wherein (1) said microcontroller establishes communication with a computer via said communication port, and (2) uploads said logging event data to said computer;

said alphanumeric display comprising a backlit LCD display element;

said portable hand-held oxygen monitor further including a gas sampling probe connectable to said gas port, said gas sampling probe comprising a flexible gas-carrying tube having a rigid probe tip at a first end and a quick-connect fitting at a second end, said quick-connect fitting being interlockable with a counterpart quick-connect fitting mounted to said gas port, said quick-connect fittings being capable of swiveling relative to each other when connected together, thereby preventing twisting and kinking of said gas-carrying tube;

said rigid probe tip being configured to probe to the centerline of a pipe structure to be welded;

said rigid probe tip being at least approximately 100 mm in length and having an outside diameter of not more than approximately 5 mm; and said rigid probe tip is at least approximately 160 mm in length and having an outside diameter of not more than approximately 2 mm, with an inside diameter of approximately 1 mm.

20. A method for monitoring oxygen in a weld zone established between two pipes to be welded together using an inert gas welding operation, comprising:

providing a portable hand-held oxygen monitor comprising:

a monitor housing, said housing having a front, a back, a top, a bottom, and two sides extending between said front and back and said top and bottom;

said housing having a hand-holding portion that is sized and configured to be held in the palm of a hand of a monitor user, with the user's thumb engaging by directly contacting one of said sides and the user's remaining fingers engaging by directly contacting the other of said sides;

said hand-holding portion having an average thickness dimension representing a separation distance between said front and back of said housing of approximately 1.5-2.5 inches, and an average width dimension representing a separation distance between said sides of said housing of approximately 2.5-3.5 inches;

a user interface on said front of said housing, said user interface including an alphanumeric display operable to display a gas sample oxygen level value, and one or more user interface buttons;

an audiovisual alarm comprising non-alphanumeric indicator light on said front of said housing and an audio output device within said housing, said indicator light being separate and distinct from said alphanumeric display;

a power switch on said housing;

a quick-connect gas port on said housing operable to connect said oxygen monitor to a gas sampling probe;

a digital communication port on said housing operable to connect said oxygen monitor to a computer via a data cable;

a battery charge port on said housing operable to connect said oxygen monitor to a battery charging device;

an electrochemical oxygen sensor within said housing;

a pump within said housing having a pump inlet in fluid communication with said gas port and a pump outlet in fluid communication with said oxygen sensor;

a microcontroller within said housing, said microcontroller including a microcontroller coupled to memory comprising a non-transitory computer-readable storage medium, said microcontroller being connected to said user interface, said audiovisual alarm, said digital communication port, said oxygen sensor, and said pump;

a direct current battery power source within said housing operable via said power switch and connected to provide electrical power to said monitor, and to receive electrical power from said battery charge port;

said memory of said microcontroller storing program instructions that program said microcontroller to perform program operations;

said program operations comprising implementing an oxygen monitoring mode responsive to activation of one or more of said user interface buttons, wherein (1) said microcontroller activates said pump to draw a gas sample from said gas port and deliver it to said oxygen sensor, (2) said oxygen sensor detects an amount of oxygen in said gas sample and outputs a corresponding voltage that is processed into a digital gas sample oxygen level value, (3) said microcontroller outputting said gas sample oxygen level value on said alphanumeric display, (4) said microcontroller comparing said gas sample oxygen level value to an oxygen level alarm value stored in said memory, and activating said audiovisual alarm if said gas sample oxygen level value is less than said oxygen level alarm value, said activating comprising illuminating said indicator light and generating a sound from said audio output device to alert a monitor user that is safe to weld;

said oxygen monitoring mode further comprising selectively implementing a spot monitoring mode or a continuous monitoring mode responsive to activation of one or more of said user interface buttons, said spot monitoring mode comprising obtaining a single gas sample to produce a single gas sample oxygen level value in response to activation of a spot monitoring mode user interface button, said spot monitoring mode obtaining and evaluating not more than said single gas sample for any given activation of said spot monitoring mode user interface button, and said continuous monitoring mode comprising obtaining gas samples periodically to produce corresponding periodic gas sample oxygen level values in response to activation of a continuous monitoring mode button, said continuous monitoring mode obtaining and evaluating said periodic gas samples on a continuous basis until sampling is stopped by a user;

said activating said audiovisual alarm comprising said microcontroller repetitively activating then deactivating said indicator light and said audio output device in synchronization with each other;

said program operations further comprising implementing an alarm value set mode responsive to activation of one or more of said user interface buttons, wherein said microcontroller presents a range of microcontroller-suggested numeric oxygen level alarm values to a monitor user via said user interface, and wherein said oxygen level alarm value is a number received as a user selection of one of said suggested numeric oxygen level alarm values, said suggested numeric oxygen level alarm values being presented as a step-through list of said numeric oxygen level alarm values that a user can step through until a desired oxygen level alarm value is reached;

said program operations further comprising implementing an automatic calibration mode responsive to activation of one or more of said user interface buttons, wherein (1) said microcontroller activates said pump to draw an ambient air sample from said gas port and deliver it to said sensor, (2) said oxygen sensor detects an amount of oxygen in said ambient air sample and outputs a corresponding voltage that is processed into a digital ambient oxygen level value, and (3) said microcontroller storing said ambient oxygen level value in said memory;

said microcontroller storing or computing (1) an ambient air calibration percentage value representing a known oxygen content percentage by volume for air, and (2) an ambient air calibration parts per million value representing a known oxygen content parts per million by volume for air (ppm);

said oxygen monitoring mode further comprising generating said gas sample oxygen level value as (1) an oxygen level percentage by volume value using said ambient oxygen level value and said ambient air calibration percentage value, and (2) an oxygen level ppm value using said ambient oxygen level value and said ambient air calibration ppm value;

said oxygen monitoring mode further comprising said microcontroller outputting said gas sample oxygen level value as said oxygen level percentage value and said oxygen level ppm value to said alphanumeric display, and said alphanumeric display displaying one or both of said oxygen level percentage value and said oxygen level ppm value in alphanumeric form;

said oxygen monitoring mode further comprising said microcontroller storing logging event data in said memory, said logging event data including, for each logging event, one or more gas sample oxygen level values obtained during said welding operation by said oxygen monitor in association with timestamps indicating when said gas samples were obtained, said logging event data further including welding job information input via said user interface;

said logging event data including weld site location information;

said weld site location information being determined automatically by a global positioning system inside said oxygen monitor housing;

said logging event data including an indication of whether said audiovisual alarm was activated at the time of the logging event;

said program operations further comprising implementing a computer upload mode responsive to activation of one or more of said user interface buttons, wherein (1) said microcontroller establishes communication with a computer via said communication port, and (2) uploads said logging event data to said computer;

said alphanumeric display comprising a backlit LCD display element;

said portable hand-held oxygen monitor further including a gas sampling probe connectable to said gas port, said gas sampling probe comprising a flexible gas-carrying tube having a rigid probe tip at a first end and a quick-connect fitting at a second end, said quick-connect fitting being interlockable with a counterpart quick-connect fitting mounted to said gas port, said quick-connect fittings being capable of swiveling relative to each other when connected together, thereby preventing twisting and kinking of said gas-carrying tube;

said rigid probe tip being configured to probe to the centerline of a pipe structure to be welded;

said rigid probe tip being at least approximately 100 mm in length and having an outside diameter of not more than approximately 5 mm; and said rigid probe tip is at least approximately 160 mm in length and having an outside diameter of not more than approximately 2 mm, with an inside diameter of approximately 1 mm;

said method comprising:

invoking said alarm value set mode to set said oxygen level alarm value;

invoking said automatic calibration mode to obtain an ambient air sample and generate said ambient oxygen level value;

connecting said probe to said gas port inserting said probe tip through a root gap between said pipes to be welded into said weld zone;

invoking said oxygen monitoring mode to obtain at least one gas sample from within said weld zone and (1) generate a corresponding gas sample oxygen level value, (2) display said gas sample oxygen level value on said alphanumeric display as both an oxygen level percentage by volume value and an oxygen level ppm value, and (3) activate said audiovisual alarm if said gas sample oxygen level value is less than or equal to said oxygen level alarm value;

invoking said logging to create at least one logging event that stores logging event data, said logging event data including said at least one gas sample oxygen level value obtained during said welding operation by said oxygen monitor in association with at least one timestamp indicating when at least one gas sample was obtained, and in further association with weld-site location information and information indicating whether said audiovisual alarm was activated at the time of said logging event;

removing said rigid probe tip from said weld zone;

connecting said charge port to a separate computer; and invoking said computer upload mode to upload said logging event data to said computer.

\* \* \* \* \*